US009718595B2

(12) United States Patent
Leichner

(10) Patent No.: US 9,718,595 B2
(45) Date of Patent: Aug. 1, 2017

(54) CONTAINER MADE FROM A COMPOSITE OF ALUMINUM FOIL AND POLYMER AND USED FOR ANALYTICAL AIDS, AND METHOD FOR PRODUCING

(71) Applicant: Roche Diagnostics Operations, Inc., Indianapolis, IN (US)

(72) Inventor: Wilhelm Leichner, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 947 days.

(21) Appl. No.: 13/928,088

(22) Filed: Jun. 26, 2013

(65) Prior Publication Data

US 2013/0284624 A1    Oct. 31, 2013

Related U.S. Application Data

(63) Continuation of application No. PCT/EP2011/073940, filed on Dec. 23, 2011.

(30) Foreign Application Priority Data

Dec. 27, 2010  (EP) ..................................... 10016099
Dec. 27, 2010  (EP) ..................................... 10016100
Apr. 13, 2011  (EP) ..................................... 11003111

(51) Int. Cl.
*B65D 81/02* (2006.01)
*A61B 5/151* (2006.01)
*A61B 5/157* (2006.01)
*A61B 5/15* (2006.01)

(52) U.S. Cl.
CPC ............ *B65D 81/025* (2013.01); *A61B 5/157* (2013.01); *A61B 5/150022* (2013.01);
(Continued)

(58) Field of Classification Search
CPC  B32B 7/04; B32B 7/045; B32B 15/00; B32B 15/04; B32B 15/046; B32B 15/08;
(Continued)

(56) References Cited

U.S. PATENT DOCUMENTS 4,533,576 A     8/1985  Tanahashi et al.
5,209,352 A *   5/1993  Light ...................... G03C 3/00
                                                      206/391
(Continued)

FOREIGN PATENT DOCUMENTS

CA       2 753 113 A1    8/2010
CN       1243041 A       2/2000
(Continued)

OTHER PUBLICATIONS

International Preliminary Report on Patentability; PCT/EP2011/073940; Jun. 27, 2013.

*Primary Examiner* — J. Gregory Pickett
*Assistant Examiner* — Brijesh V. Patel
(74) *Attorney, Agent, or Firm* — Bose McKinney & Evans LLP

(57) ABSTRACT

A container at least to some extent composed of a sheet of composite material, where the composite material includes an aluminum foil with a first and a second surface side, a first polymer layer, bonded to at least one of the two surface sides, where the aluminum foil covers, by way of the polymer layer, at least one aperture of a holder, where the composite material and the holder together form the container, where the holder accepts at least one analytical aid in a cutout, where the aluminum foil has been molded.

20 Claims, 9 Drawing Sheets

(52) U.S. Cl.
CPC ...... *A61B 5/15029* (2013.01); *A61B 5/15146* (2013.01); *A61B 5/15151* (2013.01); *A61B 5/15161* (2013.01); *A61B 5/15176* (2013.01); *A61B 5/150358* (2013.01); *A61B 5/150572* (2013.01); *A61B 5/150412* (2013.01); *A61B 5/150503* (2013.01)

(58) Field of Classification Search
CPC ......... B32B 27/00; B32B 27/08; B32B 27/32; B32B 27/36; B65D 17/501; B65D 41/045; B65D 51/20; B65D 77/2024; B65D 81/025; B65D 2251/0015; B65D 2251/0093; A61B 5/1411; A61B 5/157; A61B 5/15029; A61B 5/15146; A61B 5/15151; A61B 5/15161; A61B 5/15176; A61B 5/150022; A61B 5/150358; A61B 5/150412; A61B 5/150503; A61B 5/150572
USPC .............. 206/305; 53/397; 220/359.1–359.4; 215/232, 329, 341, 347, DIG. 2
See application file for complete search history.

(56) References Cited

U.S. PATENT DOCUMENTS

| | | | |
|---|---|---|---|
| 5,910,138 A | 6/1999 | Sperko et al. | |
| 7,604,592 B2 * | 10/2009 | Freeman | A61B 5/1411 600/309 |
| 2003/0059350 A1 | 3/2003 | Sacherer | |
| 2005/0048307 A1 * | 3/2005 | Schubert | B32B 15/08 428/607 |
| 2006/0074351 A1 * | 4/2006 | Allen | A61B 5/150511 600/583 |
| 2006/0196031 A1 * | 9/2006 | Hoenes | A61B 5/1411 29/432 |
| 2009/0010802 A1 * | 1/2009 | Joseph | A61B 5/1411 422/22 |
| 2009/0257911 A1 | 10/2009 | Thomas et al. | |
| 2010/0174211 A1 * | 7/2010 | Frey | A61B 5/1411 600/583 |
| 2010/0213193 A1 * | 8/2010 | Helmlinger | B32B 15/08 220/200 |

FOREIGN PATENT DOCUMENTS

| | | |
|---|---|---|
| CN | 1283089 A | 2/2001 |
| DE | 198 54 316 A1 | 10/1999 |
| EP | 0 951 939 A2 | 10/1999 |
| EP | 0951939 A2 | 10/1999 |
| EP | 1 360 935 A1 | 11/2003 |
| EP | 1 813 220 A1 | 8/2007 |
| JP | 59-26460 A | 2/1984 |
| JP | 2007-290731 A | 11/2007 |

* cited by examiner

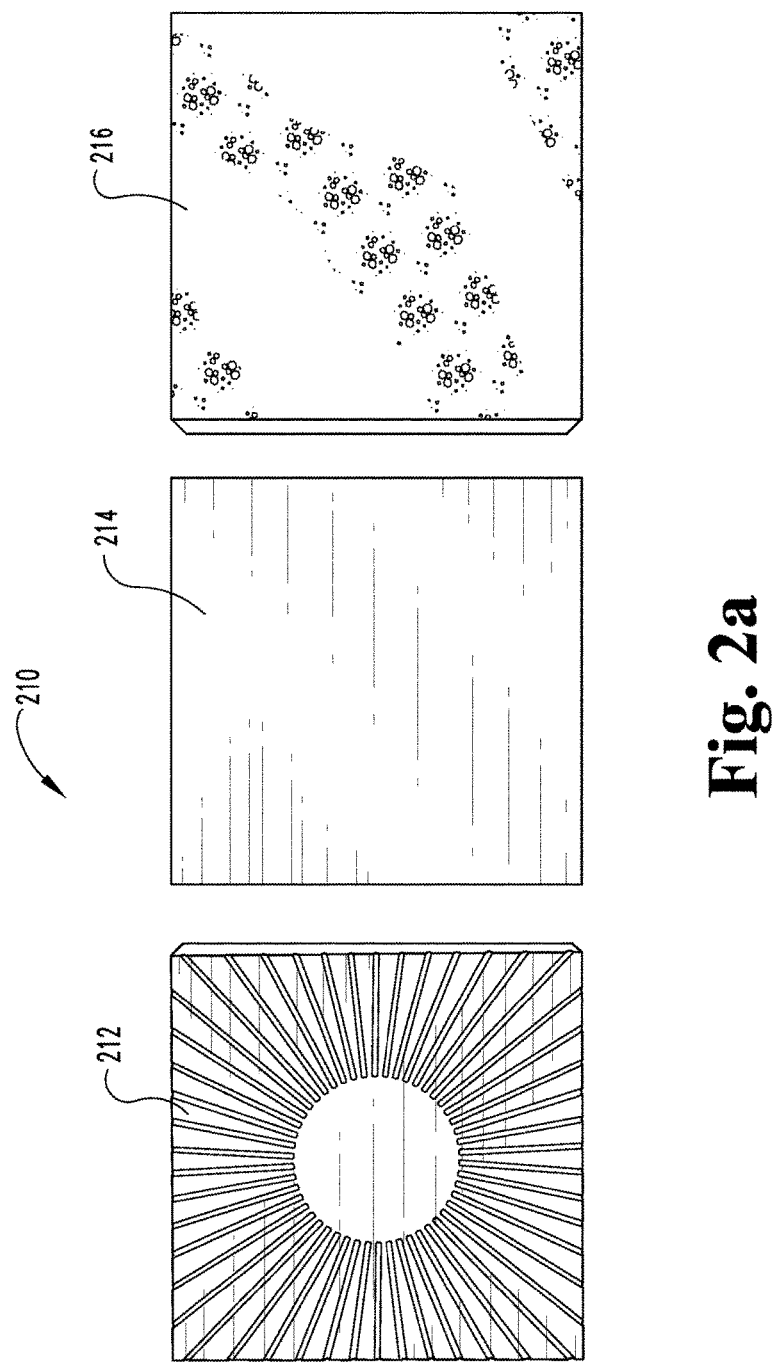

CONTAINER MADE FROM A COMPOSITE OF ALUMINUM FOIL AND POLYMER AND USED FOR ANALYTICAL AIDS, AND METHOD FOR PRODUCING

RELATED APPLICATIONS

This application is a continuation of PCT/EP2011/073940, filed Dec. 23, 2011, which claims priority to EP10016099.3, filed Dec. 27, 2010; EP10016100.9, filed Dec. 27, 2010; and EP11003111.9, filed Apr. 13, 2011, all of which are hereby incorporated by reference in their entireties.

BACKGROUND

The invention is within the field of containers for, or packaging for, analytical aids, in particular for magazines, specifically magazines for analytical sensors for the measurement of body fluid parameters, for example in a body fluid of a user. The invention relates to a process for the production of a container in particular designed to permit acceptance of an analytical aid, in particular of hydrophilic sensors, and sterile packaging of these.

The prior art discloses containers or packaging, also termed magazines, for sensors or for other articles that are to be kept sterile. The particular emphasis here is placed on ensuring sterility of said articles over a maximum period. Sterility is particularly important for articles that are intended to penetrate into the human body, examples being analytical aids.

Packaging for food or drink often uses metal composites, and particularly often uses aluminum-containing composites, with the aim firstly of providing packaging that meets food hygiene requirements, but also of producing packaging that is not excessively heavy but that is nonetheless sufficiently stable, in particular stackable, and airtight.

This type of packaging is disclosed by way of example in the documents WO 2007/029755 and EP-A-1 640 277, where a thermoplastic material is applied on an aluminum surface in order to bring about sufficient stability for the storage of food or drink comprising carbonic acid. Although said containers ensure that stability is sufficient for the everyday handling of the food or drink, they have the disadvantage that they have to have a minimum thickness in order to ensure that stability is adequate for handling by a user and in order to withstand not only the stresses caused by direct exposure to the food or drink but also the stresses caused by the environment, for example during transport.

Other packaging known from the medical sector ensures that articles to be kept sterile are packaged hermetically: medicaments to be packaged under sterile conditions are often packaged in aluminum blisters, as described in NL-A-1023464, and here again adequate stability has to be ensured because the blisters are subject to everyday handling by patients who in some instances may have motor disabilities.

WO 2010/094426 describes the production and packaging of a medical aid where aluminum-containing materials are likewise described for keeping the medical aids sterile. A laser-welding process is moreover described for sealing medical aids under sterile conditions in that type of packaging. However, that document gives no more detailed description of the nature of the materials and their processing.

In particular when integrated analytical aids are provided, as described in WO 2010/094426, and these are used not only for the provision of body fluid but also for analysis thereof, it is important to ensure that these highly sensitive aids can be suitably stored: on the one hand, it is important to select packaging which can ensure that the analytical aids are sufficiently sterile, but it is also important to prevent impairment of the highly sensitive surfaces of the analytical aids by the packaging.

SUMMARY

Embodiments incorporating the present invention overcome, at least to some extent, at least one of the disadvantages resulting from the prior art. A container is disclosed which ensures that analytical aids can be stored with maximum simplicity and efficiency: the analytical aids are intended to be packaged firstly so that they have protection and secondly so that they are easily accessible, the aim being not only to ensure that the aids can be stored for a long time and can function for a long time but also that they are subject to minimum impairment when used. A process for the production of this type of container is also disclosed.

In a first aspect of this disclosure, a container is at least to some extent composed of a sheet of composite material, said extent preferably being at least 10%, preferably at least 20%, preferably at least 30%, preferably at least 50%, and particularly preferably at least 70%, of the external surface, based in each case on the total external surface of the container, where the composite material includes:
  an aluminum foil with a first and a second surface side,
  a first polymer layer, bonded to at least one of the two
    surface sides,
where the aluminum foil covers, by way of the polymer layer, at least one aperture of a holder, where the composite material and the holder together form the container, where the holder accepts at least one analytical aid in a cutout.

Another aspect of this disclosure provides a container at least to some extent composed of a sheet of composite material, said extent preferably being at least 10%, preferably at least 20%, preferably at least 30%, preferably at least 50%, and particularly preferably at least 70%, of the external surface, based in each case on the total external surface of the container, where the composite material includes:
  an aluminum foil with a first and a second surface side,
  a first polymer layer, bonded to at least one of the two
    surface sides,
where the aluminum foil covers, by way of the polymer layer, at least one aperture of a holder, where the composite material and the holder together form the container, where the holder accepts at least one analytical aid in a cutout, where the aluminum foil has been molded, in particular pressed or deep-drawn.

In one embodiment of the container, the sheet of composite material covers from 5 to 70%, preferably from 10 to 50%, particularly preferably from 15 to 30%, of the total external surface of the container. The arrangement particularly preferably has the composite material radially at the external surface of the container.

The container surrounds at least one analytical aid, preferably in the form of packaging, with the aim of separating the analytical aid from the environment. The term separation is preferably used to mean that the packaging surrounds the analytical aid on all sides and thus separates it entirely from the environment, with the aim, by way of example, of ensuring that packaging is achieved under sterile conditions. The container is composed at least to some extent of a holder which accepts the at least one analytical aid in at least one cutout. The holder has the function of surrounding at least one analytical aid at least to some extent and of thus protecting it from its environment. The aim here is that the holder firstly protects the analytical aid from mechanical effects, and secondly can keep the analytical aid sterile. The holder should moreover provide a possibility, which is also available when a plurality of analytical aids are stored, of successfully transporting same, and of rendering the same easily accessible to the user or optionally to a usage device.

The holder can have various shapes. By way of example, the holder can have a rectangular, cylindrical, or spherical shape, in particular the shape of a circle or of a disk. The holder preferably has at least one basal element, for example in the form of a frame for the storage of analytical aids. The frame can serve to facilitate handling of the holder and for stabilization of same. Located in or on the frame of the holder there is at least one cutout for the acceptance of at least one analytical aid. As described in detail below, there can be a plurality of cutouts located in the holder. Said cutouts can accept one or more analytical aids or other aids that are useful for the use of the holder. Said at least one cutout serves to surround the at least one analytical aid at least to some extent, with the aim of permitting protected and preferably sterile storage of same for its subsequent use. The cutout can have a plurality of walls which surround the analytical aid. The walls here can enclose at least a portion of a space into which the analytical aid is introduced. The space here can assume any of the conceivable shapes, as long as it is suitable for accepting the analytical aid and for rendering same accessible for use thereof. The at least one cutout may have an elongate shape, appropriate to the elongate shape of the preferred analytical aid. The design of the at least one cutout can by way of example be spherical, cylindrical, or preferably rectangular. The cutout should have at least one aperture for the charging of analytical aids to the cutout. Said aperture can have been introduced at any desired side of the cutout, preferably at a side to which there is external access. It is preferable that the holder has at least two apertures, preferably located in, or adjacent to, the at least one cutout. It is particularly preferable that the cutout has an aperture at the transverse sides of the rectangular body. In a possible alternative, the location of the apertures can also be at an elongate side and at a transverse side, or alternatively only at the elongate sides. The apertures here can serve various purposes: by way of example, the elongate aperture can serve for introduction of the analytical aid into the cutout and thus into the subsequent container. The aperture(s) in the transverse side can by way of example serve for the use of the analytical aid during its subsequent use. The design of an aperture can therefore be intended to provide the analytical aid, and a further aperture can therefore be intended to serve for acceptance of an element of a usage device, with the aim of conducting the analytical aid into a usage position. However, other embodiments are also conceivable.

If there is more than one cutout located in the holder, the arrangement can preferably have these alongside one another in the frame of the holder. Designs of the holder with cutouts mutually superposed or in series are also conceivable. The arrangement preferably has the cutouts alongside one another in the shape of a circle. It is particularly preferable that the cutouts have apertures parallel to the area of the circle and perpendicular to the area of the circle. In one embodiment, the cutouts are elongate, designed in the form of a rectangular body, arranged with their elongate dimension radially at the external side of the disk-shaped holder.

The positioning of the analytical aid in the cutout is preferably such that it has minimum contact with the frame of, or with the walls of, the cutout. This is particularly preferable when the analytical aid comprises regions which are intended, prior to their use, to protect it from contact with other articles, liquids, or other environmental factors. To this end, the analytical aid can comprise a region which serves for contact with the holder, permitting positioning of the analytical aid in the cutout while avoiding any other effect.

The holder can have been produced from various materials. It is preferable to use materials which, while having adequate mechanical stability in order to provide protection from impacts and to permit handling by a user, are not too heavy to permit storage of a maximum number of analytical aids. The material of the holder, or of the container, should moreover have good resistance to high-energy radiation (for example beta-radiation, gamma-radiation, or X-ray radiation), if the intention is to keep the analytical aids sterile. Adequate stability of the container for the planned period of use should be ensured, and this also applies after irradiation, and adequate ability to prevent ingress of microbes over said period should be ensured. This period depends on the use of the analytical aid and can be a number of years. The holder can therefore be composed of any material that is known by the person skilled in the art to achieve these properties: by way of example, the holder can have been manufactured from sheetmetal, for example from steel sheet or from aluminum sheet. As an alternative, or in addition, the holder can have been manufactured from a plastic, an example being a polycarbonate (PC) or a copolyester, and another example being polyphenyl sulfone (PPSU). Composite materials made of metal and of plastics are also conceivable.

An aluminum foil is used for the sealing of the apertures of the holder, or of the container, and forms, at least with a polymer layer, a sheet of composite material.

An aluminum foil is an aluminum-containing product which has a markedly greater dimension in a first spatial direction, also termed length of the aluminum foil, and in a second spatial direction, also termed width of the foil, than in a third spatial direction, also termed the thickness. The aluminum-containing foil can also comprise further constituents, for example further metals, such as iron, copper, gold, or silver, or nonmetallic materials, or a mixture thereof. It can moreover also comprise other or further materials, examples being pigments, for example in the form of dyes, or by way of example fillers, for example in the form of organic compounds. It is preferable that the aluminum foil is composed of at least 95% by weight, preferably 97% by weight, and particularly 99% by weight, based in each case on the aluminum foil, of aluminum. It is preferable that the aluminum foil is composed of from 90 to 100% by weight, particularly from 95 to 100% by weight, very particularly from 97 to 100% by weight, of aluminum.

The dimension of the foil in a first and a second spatial direction can be several meters, whereas the dimension in the third spatial direction, also termed thickness or cross section, can by way of example be only a few mm or p.m. It is preferable that the aluminum foil has a uniform thickness: by way of example, the deviation of the cross section of this type of aluminum foil is a few μm, preferably from 0.1 to 10 μm, particularly preferably from 0.1 to 3 μm.

The container is obtainable in that a first polymer layer has been provided on at least one side of the aluminum foil. The polymer layer can be provided in various ways on the aluminum foil or adjacent to the aluminum foil: by way of example, the polymer layer can be a polymer foil adhesive-bonded to the aluminum foil. The adhesive bonding can be achieved by way of example via melting of the polymer foil, where the polymer foil is first brought into contact with the aluminum foil and then both are heated and compressed. In an alternative, it is also possible that there are further layers located between the aluminum foil and the polymer layer: by way of example the arrangement can have, between the aluminum foil and the polymer layer, an adhesive layer which serves to bond the foil to the layer. Equally, the polymer layer, or else the polymer foil, can have been rendered adhesive. This is mostly achieved via copolymerization of functional monomers which have functional groups which can react chemically with the surface of the aluminum foil. If a sheet of composite material is used and the material has been molded, in particular pressed or deep-drawn, prior to formation of the container, possible alternatives provide the polymer layer prior to the pressing or deep-drawing of the aluminum foil or after the molding of the aluminum foil.

It is preferable that the aluminum foil or the sheet of composite material is molded, in particular pressed or deep-drawn prior to formation of the container. It is further preferable that at least the first polymer layer is bonded to the aluminum foil prior to the molding of the aluminum foil.

The molding process preferably establishes the profile of the sheet of composite material or of the aluminum foil at the site that undergoes the forming process. It is possible by way of example that the molding process introduces a crease or a sharp bend into the composite material or, respectively, aluminum foil, which in other respects is a sheet. The forming process can fix the profile on either side of said sharp bend. It is preferable that, during the molding process, the sheet of composite material or of the aluminum foil is subjected to sharp bending that brings about a change in the profile of the aluminum foil in the range from 10° to 170°, preferably in the range from 30° to 150°, particularly preferably in the range from 50° to 120°. The sharp bend is preferably a discontinuity in the profile of the aluminum foil or of the composite material, and preferably fixes to regions of the aluminum foil or of the composite material in an angled arrangement with respect to one another. It is preferable that at this site of sharp bending the aluminum foil or the composite material cannot be bent flexibly in the manner that remains possible in the regions not subjected to sharp bending.

It is moreover possible to achieve forming processes to different extents at various sites in the aluminum foil or in the sheet of composite material: the aluminum foil or the sheet of composite material can undergo 120° deformation at one site and 90° deformation at another site. This can be brought about by way of example in the pressing or deep-drawing process via the selection of the ram used, as explained below. By virtue of the forming process, the aluminum foil or the sheet of composite material can by way of example come into contact at more than one site with the holder. In this way it is possible by way of example to use only one aluminum foil or only one sheet of composite material to provide protective covering of apertures which extend across more than one surface, or of a plurality of apertures located in various surfaces of the holder. The procedure for the deep-drawing or pressing process is explained in more detail below in the context of the process for the production of the container.

Said molding of the aluminum foil can moreover be preceded by an embossing process, as explained in more detail below. As an alternative here, the application of the polymer layer to, or on to, the aluminum foil can take place prior to or after the embossing process.

In general terms, it is preferable in one embodiment that the first polymer layer is composed of a thermoplastic polymer. The first polymer layer can also comprise, alongside the thermoplastic polymer, further additives, mostly less than 35% by weight, preferably less than 15% by weight, and particularly preferably less than 7% by weight, based in each case on the first polymer layer. These additives can be pigments, antistatic agents, and others that are frequently processed with thermoplastic polymers with the aim of rendering properties thereof appropriate to a particular application. The first thermoplastic polymer can moreover also be composed of a mixture of two or more thermoplastic polymers differing from one another. It is moreover preferable that the melting point of the thermoplastic polymers used in this disclosure is above 50° C., with preference above 90° C., and particularly above 130° C. It is preferable that the thermoplastic polymer involves a polyester. Examples of resins of this type are products available commercially, and also mixtures of these, examples being Vitel®2100B, Vitel®2200B, Vitel®3200B and Vitel®3300B.

It is particularly preferable that the thermoplastic polymer involves straight-chain, saturated copolymers of various polyesters. It is preferable that the thermoplastic polymer comprises amounts in the range from 0 to 50% by weight, preferably in the range from 5 to 30% by weight, particularly in the range from 10 to 20% by weight, of further additives. Examples of additives that can be used are lubricants. Examples of additives are those selected from the group consisting of molybdenum sulfide ($MoS_2$), Teflon, graphite (C), copper (Cu), lead (Pb), ceramics, and plastics, or at least two thereof.

As an alternative, or in addition, the polymer layer can be hydrophilic. It is moreover possible to use an additional polymer layer that is hydrophilic. The hydrophilic nature of a polymer can be influenced via the selection of its substituents: an increase in the content of hydrophilic substituents used increases the hydrophilicity of the polymer. Preferred hydrophilic substituents are substituents selected from the group consisting of hydroxy group (—OH), hydrogensulfide group (—SH), amine group (—$NH_2$, —NRH), and acid groups (—OOH), or else at least two thereof. It is preferable that the polymers used to construct the polymer layer have from 10 to 80% by weight content of hydrophilic substituents, preferably from 20 to 70% by weight, particularly from 30 to 60% by weight.

In general terms, the first and the further polymer layer can be applied to the aluminum foil by any method that is known to, and appears suitable to, the person skilled in the art: the polymer can be applied in the form of melt, in the form of solution in a solvent, or from a combination of melt and solution. Examples of methods that can be used are spraying, spincoating, doctoring, or spreading, or a combination of at least two of these methods. It is preferable that the first polymer layer or the further polymer layer is provided by using a doctor to apply a dissolved polymer. Doctor systems and solvents known to the person skilled in the art can be used for this purpose. As an alternative, the application of the polymer layer can include melting and solidification of the first polymer layer or of the further polymer layer, or of both. This can preferably result in penetration of the polymer melt into the cavities of a substrate, generally in this case the surface of the aluminum foil. The solidification of the polymer melt in the cavities anchors the polymer layer on and in the substrate. A term often used for this is sealing or heat-sealing. A process of this type can be used for the bonding of the coated aluminum foil to further materials, for example to the holder, in order to form a container in the form of a magazine. The heat-sealing process is preferably carried out at a temperature of from 160 to 280° C., preferably from 200 to 250° C. The selection of the temperature depends on the constitution of the materials to be melted: many plastics having a melting point of from 220 to 240° C. As an alternative or supplement thereto, there can be functional groups provided in the thermoplastic polymer which can enter into chemical bonding with the surface of the substrate. The term adhesion is often used for this. Bonding can take the form of either sealing or adhesion, or a combination of sealing and adhesion. It is preferable here that the bonding is achieved with minimum use of solvent, or indeed without use of solvent: it is preferable in this disclosure that the amount used of a solvent in the bonding process is less than 10% by weight, with preference less than 1% by weight, and particularly less than 0.1% by weight, based in each case on the thermoplastic polymer. It is moreover preferable in this disclosure that the amount used in the bonding process of a low-molecular-weight adhesive that is liquid at a temperature as low as 30° C. is minimized, with preference being less than 10% by weight, with preference less than 1% by weight, and particularly less than 0.1% by weight, based in each case on the thermoplastic polymer, or indeed zero. In one embodiment, the container therefore includes a composite material which comprises less than 1% by weight, preferably less than 0.1% by weight, and particularly preferably less than 0.01% by weight, of a solvent, based in each case on the thermoplastic polymer of the composite material. In another embodiment, the container of the invention moreover includes a composite material which comprises less than 1% by weight of a low-molecular-weight adhesive, preferably less than 0.1% by weight, and particularly preferably less than 0.01% by weight, based in each case on the thermoplastic polymer of the composite material.

It is moreover preferable that the amount used of a solvent in the bonding process is in the range from 0.01 to 10% by weight, with preference in the range from 0.01 to 1% by weight, and particularly in the range from 0.01 to 0.1% by weight, based in each case on the thermoplastic polymer. It is moreover preferable in this disclosure that the amount used of a low-molecular-weight adhesive in the bonding process is minimized, with preference being in the range from 0.01 to 10% by weight, with preference in the range from 0.01 to 1% by weight, and particularly in the range from 0.01 to 0.1% by weight, based in each case on the thermoplastic polymer, or that the amount used of low-molecular-weight adhesive that is liquid at a temperature as low as 30° C. is zero. In one embodiment, the container of this disclosure therefore includes a composite material which comprises an amount in the range from 0.005 to 1% by weight of a solvent, preferably an amount in the range from 0.005 to 0.1% by weight, and particularly preferably an amount in the range from 0.005 to 0.01% by weight, based in each case on the thermoplastic polymer of the composite material. In another embodiment, the container moreover includes a composite material which comprises an amount in the range from 0.001 to 1% by weight of a low-molecular-weight adhesive, preferably an amount in the range from 0.001 to 0.1% by weight, and particularly preferably an amount in the range from 0.001 to 0.01% by weight, based in each case on the thermoplastic polymer of the composite material.

In one preferred embodiment, the maximum thickness or maximum cross section of the aluminum foil is from 1 to 100 μm, preferably from 5 to 70 μm, particularly from 10 to 30 μm. The maximum thickness of the aluminum foil is very particularly preferably from 15 to 25 μm.

The thickness of the aluminum foil is also within the stated ranges in the optionally introduced embossments. The optional embossments can merely bring about multiple alterations of the profile of the aluminum foil, and this can increase the dimension of the profile of the aluminum foil or of the sheet of composite. By way of example, the aluminum foil can assume a corrugated or undulating profile by virtue of the embossment. If the cross section is measured across this embossed region, which comprises corrugation peaks and corrugation troughs, the cross section can deviate markedly from that of the original aluminum foil: after the embossing process, the aluminum foil can comprise a region with overall cross section in the range from 10 to 500 μm, preferably in the range from 20 to 200 μm, particularly preferably in the range from 30 to 120 μm.

In one embodiment, the composite material includes a further polymer layer. The further polymer layer can likewise be composed of a thermoplastic polymer. The first polymer layer and the further polymer layer can be composed of the same, or different, thermoplastic polymers. The statements made in relation to thermoplastic polymers in the context of the first polymer layer also apply to the further polymer layer, and vice versa. The location of the further polymer layer can by way of example be on the opposite side of the aluminum foil on which the first polymer layer has been applied. As an alternative, the location of the further polymer layer can be on the same side as the first polymer layer. In addition to the first and second polymer layer, there can also be further layers located on the first or second side of the aluminum foil, the examples being layers made of aluminum, of wax, of a coating material, or of other materials.

In one embodiment of the container, the first polymer layer or the further polymer layer is a thermoplastic polymer, often also being made of a resin, preferably of a polyester, of a wax, or of a mixture thereof. A resin is a hydrocarbon compound that is not soluble in water. Substances considered to be a resin are inter alia all of those known as synthetic polymers to the person skilled in the art. Examples of resins are urea resins, alkyde resins, epoxy resins, melamine resins, phenolic resins, polyester resins, polyurethane resins, polyamide resins, and vinyl resins, and also at least two thereof. These various resins comprise different starting substances for the production of the individual resins. Production of the synthetic polymers comprises reaction of the starting substances in a condensation reaction or addition reaction to give the various resins. If starting substance and reaction conditions are appropriate, the plastics can be processed in a polymerization reaction with subsequent hardening to give thermoplastics or thermosets. It is preferable that the polymer layer uses polyester resins or alkyde resins, or a mixture thereof. It is also possible to use natural resins as an alternative to, or in combination with, the synthetic polymers.

Waxes in this disclosure are hydrocarbon compounds which above 40° C. melt without the composition. There can also be polyesters among these. A distinction is drawn between plant-derived, animal-derived, and synthetic waxes: the lipids comprise plant-derived and animal-derived waxes. Examples of synthetic waxes are paraffin, polyethylenes, and also copolymers thereof.

In one embodiment, the thermoplastic polymer, preferably a polyester, is preferably one selected from the group consisting of a polycarbonate, a polyethylene naphthalate, a polybutylene terephtalate, a polyethylene terephtalate, and mixtures of two or more thereof.

In one embodiment, the thermoplastic polymer, preferably a polyester, is with preference one selected from the group consisting of a polycarbonate, a polyethylene naphthalate, a polybutylene terephthalate, a polyethylene terephthalate, and a cellulose nitrate, and mixtures of two or more thereof.

It is moreover preferable that the first or further polymer layer comprises molybdenum sulfide ($MoS_2$). It is preferable that the content of $MoS_2$ in the first or further polymer layer is in the range from 1 to 35% by weight, particularly in the range from 2 to 30% by weight, very particularly in the range from 5 to 25% by weight. It is possible to admix one or more further substances, for example in the form of lubricant, with the thermoplastic polymer. The further substances can by way of example be those selected from the group consisting of graphite, copper, lead, ceramics, and plastics, or at least two thereof.

The polymer layer can assume various functions in the process for the production of a container and for the storage of analytical aids: the polymer layer can, if it is provided prior to the pressing of the aluminum foil, exert an influence on the behavior of the aluminum foil during the pressing procedure. If the polymer layer has a certain brittleness, it can provide increased hardness to the soft aluminum in the aluminum foil. This can have a favorable effect on the extensibility of the aluminum foil.

The aluminum foil provided in this context preferably has linear regions of embossments. The embossments can by way of example be introduced by using an embossing ram with a relief effect on the embossing surface, in order to obtain the regions of increased thickness. Said relief effect can by way of example comprise a sequence of corrugations in the form of elevations, or of elevations and depressions. However, it is also possible to use other types of relief effects, for example triangular, preferably acute-angled triangular, relief effects, where the acute angle preferably points toward the surface of the foil. By virtue of said elevations and depressions in the surface of the embossing ram it is possible to impress embossment patterns into surfaces of the aluminum foil, as long as the material of the relief effect on the embossing ram is harder than the surface of the material to be embossed.

These types of relief effects on an embossing ram use by way of example a steel surface. When the embossing ram with its relief effect is forced on to the softer material, such as foam, and this material is pressed against a smooth underlay, the pattern of the embossment relief effect is transferred from the embossing ram to the surface of the material to be embossed. This produces a minor-image relief pattern on the material to be embossed. In this way it is possible by way of example to introduce a pattern of increased- and decreased-thickness regions into the material to be embossed. When said pattern comprising depressions and elevations is introduced on to the aluminum foil, the elevations are first to reach the surface of the aluminum foil and they force material, in this case aluminum, in a different spatial direction, in such a way that on the other side there is a depression, and consequently a cavity, in the relief effect on the ram.

In one embodiment, the container is obtainable from an aluminum foil with embossments. The embossments have preferably been introduced in linear form into the aluminum foil, and preferably form a radiant ring made of three or more linear embossments. These linear embossments, also termed linear regions, mostly proceed outward from an imaginary center. The term linear in this disclosure means that, by way of an elongate region, the dimension of which is many times greater in one direction than in a second direction, the impressed pattern exhibits an alteration in the third spatial direction, when compared with the original foil. Said depression is delimited by way of example parallel to, or else obliquely with respect to, its elongate dimension, by relief elevations. This pattern can repeat parallel to, or perpendicular to, or obliquely with respect to, the elevations, thus giving a plurality of linear regions. Arrangement of the elongate relief elevations parallel to, or obliquely with respect to, or perpendicularly to, one another produces various shapes of a relief effect with linear regions. If, by way of example, the arrangement has the elevations parallel to one another, it is then possible to obtain linear regions that run continuously across the material. If, by way of example, the arrangement has the elevations obliquely with respect to one another, it is possible to obtain a relief pattern having linear regions arranged radially in the material.

In one embodiment, the container is obtainable from an aluminum foil where the linear regions have been provided radially in the aluminum foil. If the arrangement has the linear or radial regions immediately adjacent to one another, a circular arrangement of the linear regions is obtained. This embodiment of the process provides an aluminum foil where the linear regions form a circular area. If, by way of example, the linear regions have an unembossed region in the center of their radial arrangement, the consequent arrangement of the linear regions has the shape of a ring.

The container is obtainable by molding, preferably pressing or deep-drawing, of the aluminum foil, preferably with at least one embossment.

The container is also obtainable by molding, preferably pressing or deep-drawing, the aluminum foil, preferably with at least one embossment, where a ram preferably acts on the at least one embossment. The molding process achieves a change in the shape or profile of the material that is to undergo the forming process. Various methods can be used for this, and these are known to the person skilled in the art for the forming process using aluminum foils. The molding process can inter alia be a bending, rolling, pressing, or deep-drawing process. By way of example, in the pressing or deep-drawing process a ram is forced on to the material to be pressed, and into a press mold. There can be a gap of varying size between ram and press mold, depending on the design of the ram and of the press mold. This gap represents the space available, when the ram is forced into the press mold, to the material that is to undergo the forming process. The forces acting during the forming process on the material that is to undergo the forming process are dependent not only on the design of the press mold and of the ram but also on the nature, for example the thickness, of the material that is to undergo the forming process. Forces that act during the pressing process can differ from those that act during the deep-drawing process: the expression pressing procedure means that the material to undergo a forming process is forced into a prescribed shape, where the thickness and shape of the material that is to undergo the forming process can change. In the deep-drawing process, which is also termed tensile/pressure-forming, the thickness of the material that is to undergo the forming process is preferably not altered. This is achieved by way of example in that the gap is preferably selected to be wider than the thickness of the material that is to undergo the forming process. For further details relating to the molding of materials, and also to the procedure for the molding process, reference is made at this point to the following literature: "Umformtechnik, volume 3: Blechbearbeitung [Working with sheetmetal]: Springer-Verlag, ISBN 3-540-50039-1 or ISBN 0-387-

50039-1", and also "Handbuch der Fertigungstechnik [Manufacturing Technology Handbook]; Carl Hanser Verlag 1986, ISBN 3-446-12536-1".

The shape, and the material, of the ram for a forming-process system can be selected as desired, as long as hardness is adequate for the forming process, preferably the pressing process or deep-drawing process: by way of example, therefore, the ram can have a round, angular, or elliptical shape. The ram can have been manufactured from a material which is not readily deformable, and at least does not alter its shape under the conditions of the pressing process. Examples of materials from which the ram can have been molded are metals and metal mixtures, and ceramic, but it is also possible to use plastics which do not change their shape when pressure on the ram is increased. The design of the ram can be solid or else hollow. The ram has an external surface which here is also termed profile and which, during the pressing procedure, interacts with the material that is to be pressed. Interaction with a press mold also takes place during the pressing process. Said press mold interacts with the side opposite to the ram of the material to be pressed. The press mold comprises a cavity into which the ram is pressed together with the material to be pressed, mostly the aluminum foil described in more detail above. The press mold here can have a shape which is the reverse of that of the ram. It is preferable that the press mold has been designed as a ring. However, it can also be a countermold which, at least at some points, deviates from the profile of the ram.

It is preferable that the press mold has a continuous perimeter into which the material to be pressed is forced with the aid of the ram. Examples of the shape of the press mold are circular, oval, corrugated, star-shaped, and angular. The press mold is particularly preferably circular.

The container is obtainable by pressing the ram together with the aluminum foil into the press mold in such a way as to produce a depression in the aluminum foil. A press apparatus used for this purpose can by way of example be one that provides a ram and a pressing mold with shapes appropriate to one another, in such a way that the material located between ram and press mold during the pressing procedure undergoes a forming process at least in one dimensional direction. By way of example, the aluminum foil, which extends in respectively one longitudinal and lateral direction, can be pressed by the pressing procedure in a third direction, perpendicular to its original profile. The foil here can be deflected by various amounts in the perpendicular direction. By way of example, the deflection of the foil can be one or more cm, or one or more mm. In the case of certain designs of the ram and certain ways of pressing the ram into the mold, the thickness of the foil at the pressed or deep-drawing regions can be thinner than it was prior to the pressing procedure. In order to reduce tearing of the foil during the pressing or deep-drawing process, embossments can have been introduced in those regions of the foil that are to be molded. Said embossments facilitate flow of the material of the foil during the molding process, in particular during the pressing or deep-drawing process.

It is preferable that ram and press mold fit into one another so precisely that only a small distance remains between them for the material to be pressed. The diameter of the press mold here is a few μm greater than the diameter of the ram. The distance between the ram and the appropriately dimensioned mold is also termed gap dimension. By way of example, a gap dimension can be only a few μm, for example from 0.1 to 100 μm, preferably from 1 to 50 μm, particularly preferably from 15 to 40 μm. The pressing of the aluminum foil with the aid of the ram to the appropriately dimensioned mold preferably presses a depression into the aluminum foil. The depth of the depression can differ, depending on the constitution of the material and on the embossment pattern. The resultant depression preferably has a cylindrical shape. However, it can also assume any of the other shapes defined via the geometry of the ram and of the appropriately dimensioned mold.

The depth of the depression in one embodiment is in the range from 1 to 10 mm, preferably in the range from 2 to 7 mm, and particularly preferably in the range from 2 to 5 mm. The linear regions impressed in the aluminum foil facilitate the pressing procedure to give a depression which is very large in comparison with the thickness of the aluminum foil. The embossed linear regions improve the ability of the aluminum foil, along the embossments, to slide into the press mold during the pressing procedure. During the molding process, in particular during the pressing or deep-drawing process, material from the embossed region can become distributed across the region that is to undergo a forming process. After the molding process, the embossments can have been minimized, or smoothed by tension, or smoothed by pressure. The sliding process can be facilitated by further aids, for example application of a wax layer to the aluminum foil. Tearing of the aluminum foil, caused by the pressure, is thus prevented. An overall effect of this is to allow a higher pressure to be exerted on the aluminum foil, i.e. a deeper depression to be achieved in the aluminum foil, than is the case with unembossed aluminum foils. This is achieved inter alia because redistribution of material takes place within the embossed regions during the molding process, preferably a pressing or deep-drawing process, and an almost smooth foil is therefore then obtained. The folds in the embossed region are smoothed in said process.

By virtue of the depression, a geometry of the aluminum foil is created which can fit around three-dimensional articles: it is thus possible to surround holders with analytical aids, preferably with the aim of obtaining a sterile leakproof container.

For the purposes of this disclosure, analytical aids are aids which can be used in support of analytical functions described in WO 2010/094426. In particular, the analytical aids can involve medical and/or diagnostic aids, in particular aids capable of use in qualitative and/or quantitative detection of at least one analyte in a body fluid of a subject, an example being one or more of the following analytes: glucose, lactate, triglycerides, clotting parameters, and cholesterol. The body fluid of a subject can by way of example involve blood, interstitial fluid, urine, or similar body fluids. In particular, the analytical aids can be disposables, i.e. can be intended for single use. Accordingly, the analytical aids can by way of example comprise at least one puncture element, for example, in the form of a lancet, i.e. an element which is capable of producing at least one aperture in the skin of the subject. This aperture in the skin of the subject can by way of example be made in an ear lobe, a fingertip, or a lower arm of the subject. By way of example, said lancets can comprise one or more needle tips and/or sharpened tips. It is also possible to use, as an alternative, or in addition, other sharp-edged elements, such as blades, sharp-edged tips, or the like. The lancets can by way of example be produced from elongate starting materials, for example in the form of acicular lancets. However, for the purposes of this disclosure it is particularly preferable to use one or more lancets produced from materials in the form of sheets, in particular from sheetmetal.

As an alternative to, or in addition to, lancets, the analytical aids can also respectively comprise one or more test fields. These test fields comprise at least one chemical test system capable of changing a measurable property in the presence of at least one analyte to be detected. Said chemical test system capable, alone or in conjunction with the analyte and/or with further aids, of indicating the presence or—also intended to be comprised hereby—absence of the at least one analyte can have been designed in various ways. In this connection reference may be made by way of example to WO 2007/012494 A1, in which particularly moisture-resistant chemical test systems are described. The chemical test systems mentioned in said publication can also be used, individually or in combination, for the purposes of this disclosure. In particular, highly specific chemical test systems can be used, the detection provided by which reacts specifically to the at least one analyte. The at least one measurable property, the measurement of which can be used for qualitative or quantitative detection of the at least one analyte, can by way of example comprise at least one electrochemical property and/or at least one optical property.

The analytical aids can moreover also have been designed as combined test elements: it is possible by way of example to use combined test elements with at least one lancet and with at least one test field, including at least one chemical test system, where the chemical test system can be capable of changing at least one measurable property in the presence of the at least one analyte to be detected. By way of example, the test element can have been integrated directly into the lancet: by way of example, therefore, the chemical test system can be present in the end of the lancet, and/or can cover portions of the lancet. In one preferred embodiment, the analytical aid comprises a puncture element, for example in the form of a lancet, or comprises a test field for the detection of an analyte in the body fluid, or comprises both.

The arrangement here preferably has the at least one analytical aid in an analytical magazine. Analytical magazines can have a very wide variety of shapes: particular known magazines have the shape of a stack, of a disc, or of a strip. The analytical magazine is by way of example capable of accepting a plurality of analytical aids in a plurality of cutouts. An analytical magazine is therefore preferably an apparatus which can be handled as a unit, and which by way of example can comprise a shared housing, and which is in general terms capable of use in medical technology. The term analytical here means in general terms the possibility of use for the qualitative and/or quantitative detection of at least one analyte, and/or for the determination of at least one further measurable property. In particular, the term analytical can therefore mean a diagnostic property, i.e. a use for the determination of at least one property of the body and/or one constituent of the body, of a subject. The analytical magazine can accordingly be used in an analytical system. By way of example, this type of system can involve a measurement device by means of which at least one analyte, for example at least one metabolite, is qualitatively and/or quantitatively detected in a body fluid of the subject. By way of example, these systems can involve blood glucose measurement devices, as are well known commercially, an example being AccuChek® Mobile, AccuChek® Active, or AccuChek® Go.

However, it is also possible, as an alternative, or in addition, that the lancet and the test field are separate, an example being respectively at least one lancet and, separately therefrom, respectively at least one test field per cutout of the analytical magazine. These portions of the analytical aid can by way of example also be capable of separate operation, so that by way of example the lancet can be operated by an actuator of a system, with the aim of executing a puncture movement and/or a collection movement, while the test field or the test element by way of example remains unaltered, for example within the cutout: the system can by way of example be capable of carrying out a puncture movement and/or collection movement by means of the at least one lancet and/or a capillary element optionally present in the lancet, in such a way that during a puncture procedure and/or during a sampling movement body fluid can be directly accepted by the lancet. A possibility here is that firstly the skin of the subject is punctured, body fluid is collected, and then, for example during a reverse movement of the lancet, this is transferred back into the cutout, on to the test field. Other embodiments are also possible. In one embodiment, the analytical aid comprises a test field and a puncture element which are in contact with one another, with the aim of exchanging fluid with one another.

The analytical aids can comprise, as an alternative to, or in addition to, lancets and/or test fields, further elements with analytical purpose: by way of example, transfer elements and/or collection elements which serve the purpose of acceptance and/or of transport of body fluid can be present. By way of example, such transport elements and/or collection elements can be used to take blood and/or interstitial fluid from the skin of the subject and/or from a point within the body of the subject, and/or from a point on the skin of the subject, and/or can be used for transport to a test element, in particular one or more test fields. This type of transport can by way of example take place via a transport movement, by means of one or more transport elements which are movable and which can accept and transfer an amount of the specimen of the body fluid. It is also possible, as an alternative, or in addition, that there are other transport elements and/or collection elements provided, for example capillaries and/or elements with capillary effect. By way of example, these can involve closed capillaries or capillary channels, in particular capillary gaps. Another term used before for combined analytical aids which comprise at least one lancet function and at least one capillary function is microsamplers.

In another embodiment, the analytical aid has a hydrophilic coating. This can by way of example be the above-mentioned capillary channel between lancet and test field. It is also possible, as an alternative, that the lancet or the test field has at least one region that has been hydrophilically coated. This permits improved transport of the body fluid on the analytical aid.

In one embodiment of the container, there is a large number of analytical aids provided in a ring-shaped holder. This often represents use of a magazine for the analytical aids. Specifically, this involves a circular design of the analytical aids. It is therefore preferable that the magazine also assumes a circular design in the form of a disk.

It is particularly preferable that the manner of acceptance of the analytical aids in the cutouts is such that precisely one analytical aid has been accepted in one cutout. If each analytical aid itself comprises a plurality of analytical sub-aids, for example respectively at least one lancet and respectively at least one test field, it is possible by way of example that the respective at least one test field and/or the respective at least one lancet provided for a single, shared test (for example a single acceptance of body fluid and/or analysis of body fluid) have been accepted in a shared cutout. This design in which each cutout has accepted one analytical aid, for example with respectively at least one sub-aid in the form of a test field, and/or with respectively at least one sub-aid in the form of a lancet, is in particular realizable in the case of a disc-shaped magazine or else in the case of other designs of magazines, for example bar-shaped magazines. In one preferred embodiment, respectively one lancet and one test field have been arranged with respect to one another in such a way that a fluid, for example in the form of blood, adhering to the lancet, can be transferred to the test field. This can be achieved if the arrangement has the lancet and the test field mutually superposed in such a way that the liquid, in this example the blood, can be transferred directly on to the test field by exerting slight pressure on the lancet or the test field.

Another design that is possible, as alternative to a design in which each analytical aid has been accepted in a separate cutout, is one in which a plurality of analytical aids of the same type or of different type have been accepted in one cutout. An example of this type of design is a tape magazine in which a supply reel with a plurality of unused analytical aids has been accepted in a first cutout and a take-up reel with a plurality of used analytical aids has been accepted in a second cutout. Other designs are also possible.

A cutout here is in general terms an element which comprises at least one at least partially closed cavity in which the analytical aid can have been accepted. The cutout can also be termed a chamber. The cavity here can also comprise one or more apertures. The cutouts can also respectively comprise one or more sub-cutouts, and can respectively comprise one or more cutout walls which face toward an inner space with the cutouts.

Once the analytical aid has been introduced into the cutout of the holder and the apertures have been protectively covered by the aluminum foil, the container is sealed. The term sealed preferably means hermetic sealing, with the aim of enabling sterile storage of the analytical aids. The container is then hermetically sealed, preferably in a heat-sealing process. However, it is also possible to use other processes, such as laser welding processes or adhesive processes.

The polymer layer can contribute to entire or substantial avoidance of impairment of the hydrophilicity of the analytical aid during storage thereof within the container. This can be particularly important for analytical aids that are to be stored and that have a hydrophilic coating. By virtue of the selection of the materials for the container, it is possible to maximize the storage period of the analytical aid in its original condition. In another embodiment, the design of the container is such that the analytical aid is kept hydrophilic prior to use. This can by way of example be achieved by applying a polymer layer to both sides of the aluminum foil. It is preferable that a polyester layer is involved here.

In another embodiment, the thickness of the first polymer layer, or of the further polymer layer, or of both, is in the range from 0.5 to 20 µm, preferably in the range from 0.5 to 10 µm, more preferably in the range from 2 to 8 µm, and particularly preferably in the range from 3 to 6 µm.

In another aspect of this disclosure, a process for the production of a container for the storage of analytical aids is proposed, including the following steps:
provision of a holder with a plurality of analytical aids,
protective covering of at least one portion of the holder with a sheet of composite material including an aluminum foil bonded to a polymer layer, where the polymer layer faces toward the holder,
heating at least of the polymer layer, so that the polymer layer melts at least to some extent and bonds to the holder and forms a container.

In another aspect of this disclosure, a process for the production of a container for the storage of analytical aids is proposed, including the following steps:
provision of a holder with a plurality of analytical aids,
protective covering of at least one portion of the holder with a sheet of composite material including an aluminum foil bonded to a polymer layer, where the polymer layer faces toward the holder,
heating at least of the polymer layer, so that the polymer layer melts at least to some extent and bonds to the holder and forms a container, where, prior to or during the process of protective covering of at least one portion of the holder with the sheet of composite material, the aluminum foil is molded, in particular pressed or deep-drawn.

During the molding process, it is preferable that the aluminum foil is pressed or deep-drawn. This form of the forming process preferably takes place prior to the protective covering of a portion of the holder. However, it is also conceivable that the holder is manufactured from a material which renders the holder suitable for use as ram in a pressing or deep-drawing procedure for the aluminum foil. As previously mentioned, the polymer layer can be bonded to the aluminum foil prior to or after the forming process.

In another step of a process it is moreover possible to bond at least one further polymer layer directly or indirectly to the aluminum foil. Directly means direct contact of the further polymer layer with the aluminum foil, whereas in the indirect bonding process there is no direct contact between aluminum foil and further polymer layer.

In another embodiment of the process, the polymer layer is composed of a thermoplastic polymer. The thermoplastic polymer is preferably a polyester.

In another embodiment of the process, the polyester is one selected from the group consisting of: polycarbonate, polyethylene naphthalate, polybutylene terephthalate, polyethylene terephthalate, and polyester resin, and mixtures of at least two thereof.

In another embodiment of the process, the polyester is one selected from the group consisting of: polycarbonate, polyethylene naphthalate, polybutylene terephthalate, polyethylene terephthalate, cellulose nitrate, and polyester resin, and mixtures of at least two thereof.

In another aspect of this disclosure, a process for the production of a container, preferably at least to some extent from a composite including aluminum, is proposed, where the process includes the following steps:
provision of an aluminum foil,
pressing of the aluminum foil, in such a way as to produce a depression in the aluminum foil,
introduction of an analytical aid into the depression,
sealing of the container, preferably to form packaging which is intended for the analytical aid and which protects same from the environment.

The term separation is preferably used to mean that the packaging surrounds the analytical aid on all sides and thus separates it entirely from the environment, with the aim, by way of example, of ensuring that packaging is achieved under sterile conditions, and is often also gastight.

For the design of the aluminum foil, reference is made to the statements made in relation to the container of this disclosure.

The pressing process for the aluminum foil is often also termed a deep-drawing process, and preferably takes place as described above.

In the context of the design of this process, it is preferable that the term depression means a space which extends between at least two areas angled with respect to one another in the pressed aluminum foil or the pressed composite material. The areas angled with respect to one another are preferably produced by the sharp deflection of the aluminum foil at the internal side of the sharp bend during the pressing procedure. The depression here can be a feature which is formed in the aluminum foil or in the composite material by at least two surfaces preferably angled with respect to one another in the aluminum foil or in the composite material, and can be open in the other spatial directions.

The dimensions of the surfaces angled with respect to one another after the pressing process here can be in the range from 1 mm to 0.5 m, preferably in the range from 1 cm to 30 cm, particularly preferably in the range from 2 cm to 20 cm, perpendicularly to the sharp bend that is produced by the pressing process.

In this disclosure, the analytical aid is introduced into said depression. Individual analytical aids, such as those described above, can be involved here, or a large number of analytical aids can be involved. By way of example, a large number of analytical aids can be held together by a holder, as mentioned and defined above.

The sealing of the container can preferably be undertaken by adhesive bonding of the aluminum foil, as described above, or by melting of a polymer layer which has been bonded to the aluminum foil, as described above, by use of heat. It is preferable that the polymer layer is fused to the holder by melting.

The statements made in relation to the container of this disclosure are moreover equally and correspondingly applicable to the process of this disclosure for the production of a container. This is particularly true for materials and spatial designs.

BRIEF DESCRIPTION OF THE DRAWINGS

Further details and features of the invention are apparent from the following description of preferred inventive examples, in particular in conjunction with the dependent claims. The respective features here can be realized per se alone or a plurality of features can be realized in combination with one another. The invention is not restricted to the inventive examples. The figures are diagrams of the inventive examples. The same reference symbols in the individual figures here designate the same elements or designate functionally identical elements or elements which correspond to one another in terms of their function. The individual figures depict the following:

FIG. 2a is a photograph of an embossing tool with milled lower part, cover and foam;

DETAILED DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of the present invention.

Figure 1A:
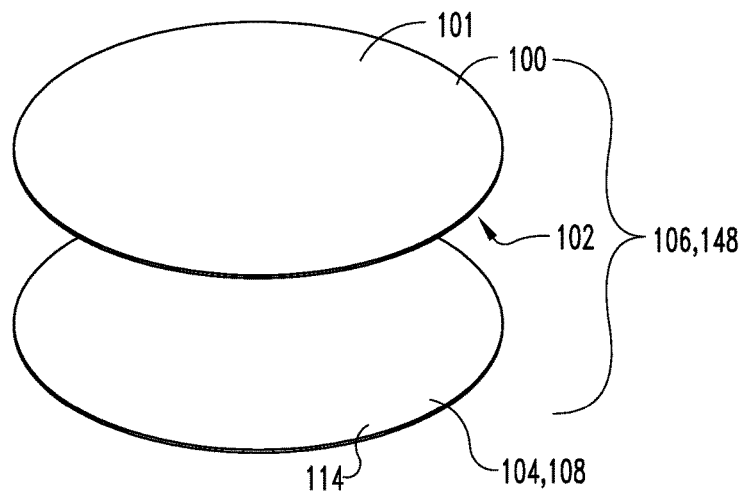
FIG. 1a is a diagram of an arrangement of an aluminum foil and of a polymer foil.

FIG. 1a is a diagram of an aluminum foil 100, the shape of which is round, and which is a portion of the container 146. Said aluminum foil 100 can be bonded on at least one of the two sides 101 and 102 to a first polymer layer 104, for example to a polymer foil 104. FIG. 1a shows only the arrangement of a polymer foil 104 on the second side 102. However, it is also possible, as an alternative or in addition, to apply the polymer foil 104, or another polymer layer 114, to the first side 101. This gives an aluminum/polymer composite 106 which below is mostly termed composite 106 or merely aluminum foil 106. There can moreover be further layers located between, above or below the foils 100, 104 shown: in the case of an aluminum foil 100, 106 that will be mentioned later, without embossments 202, there is also at least one wax layer 108 applied to the aluminum foil 100 or to the composite 106. The location of said wax layer 108 is preferably on the opposite side to the polymer layer 104, if a composite 106 with only one polymer foil 104 is involved, or on the side facing away from the holder 113, if both sides of the aluminum foil 100, 106 have been covered with polymer foil 104. However, there can also be a wax layer 108 located on each of the two sides 101 and 102 of the aluminum foil 100. There can be a further layer of a protective coating material 114 located above or below the optional wax layer 108. In one example, a coating material comprising cellulose nitrate was used as protective coating material 114. To this end, an alcoholic solution was prepared with 20% by weight of cellulose nitrate (known as Zaponlack from Carl Roth) and from 10 to 25% by weight of $MoS_2$. The amount of said protective coating material 114 applied was such that the thickness of the resultant layer was 5 µm after drying of the protective coating material 114. The protective coating material 114 can provide protection with respect to corrosion of the aluminum foil on the one hand, and with respect to mechanical load, for example during the production or use of the aluminum foil. The bonding of the aluminum foil 100 to the polymer layer 104 can, as previously mentioned, take place prior to an optional embossing step or can follow same. The bonding of the aluminum foil 100 to the polymer layer 104 creates an aluminum/polymer composite 106 in the form of a sheet-like composite material 148. This type of aluminum foil 100 or aluminum/polymer composite 106 is suitable for processing in a roll-to-roll process. However, this is not shown here.

Figure 1B:
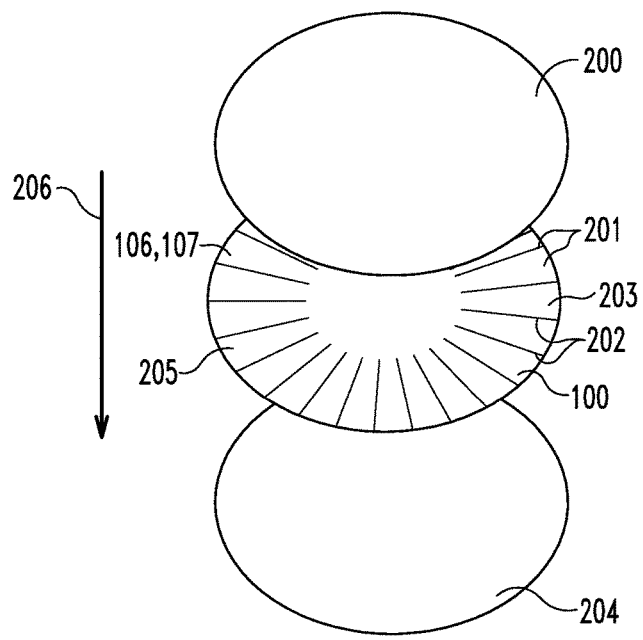
FIG. 1b is a diagrammatic arrangement of an embossed aluminum foil between a ram and a press mold.

An embossment pattern 201 is impressed into the aluminum foil 100 or the aluminum/polymer composite 106 with the aid of an embossing tool 210 from FIG. 2a. Said embossment pattern 201 is composed of a plurality of embossments 202, for example in the form of linear embossed regions 202. In this specific case, the arrangement has the linear embossments 202 radiating within a circle, and they form a circular area 203 as shown in FIG. 1b. As previously mentioned, the embossing tool 210 from FIG. 2a can be used for the embossing process. During the embossing process, a milled component 212 with a minor-image embossment pattern 201 is pressed on to the foil 100, 106, while the cover 214 is held against the other side of the foil 100, 106. A foam 216 can be placed between cover 214 and milled component 212, in order to press the foil 100, 106 into shape.

Figure 5:
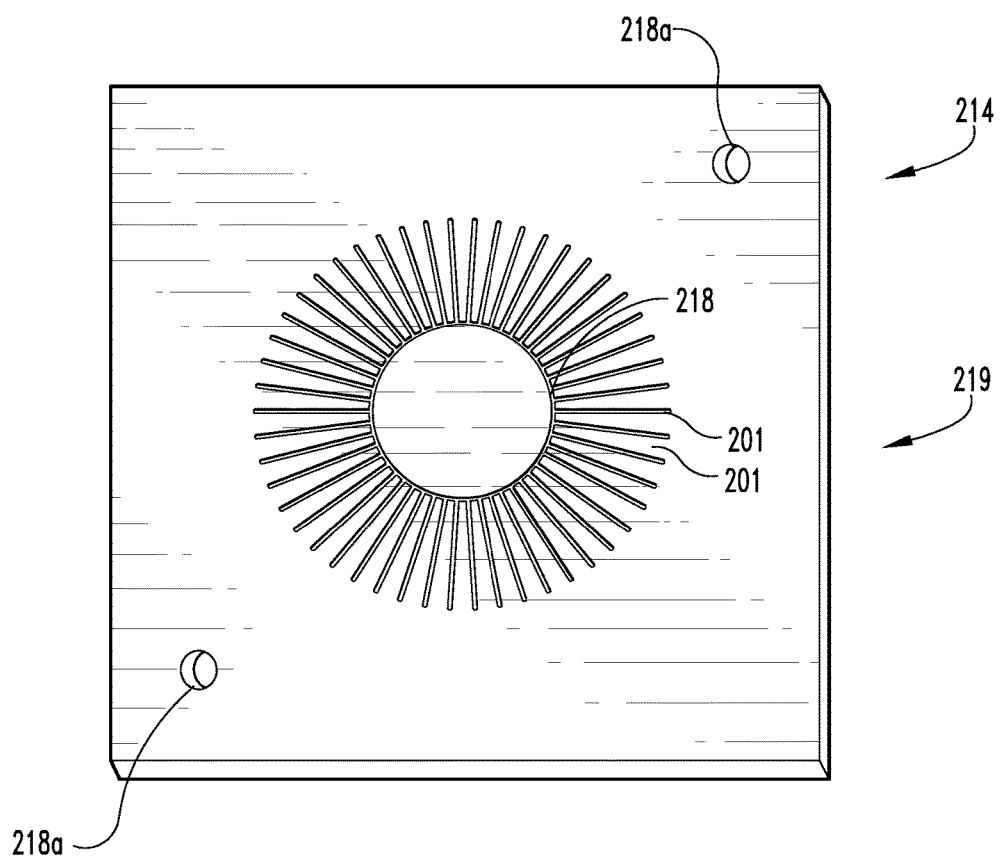
FIG. 5 is a photograph of a cover of a compressed-air press with engraved embossment pattern.
Figure 6:
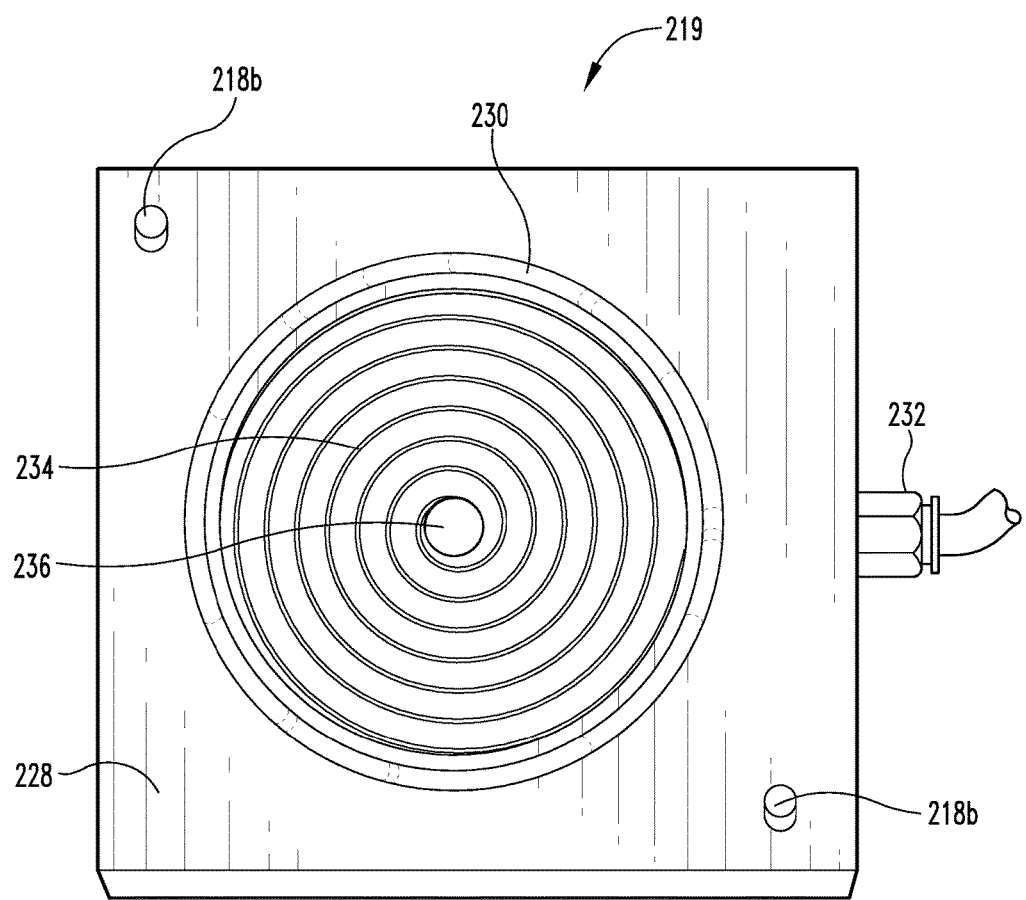
FIG. 6 is a photograph of a pressure chamber of a compressed-air press with compressed-air connection and rubber gasket.

The tooling in FIGS. 5 and 6 can provide an alternative way of introducing embossments 202 into the aluminum foil 100, 106. FIG. 5 here shows a cover 214 for a compressed-air press 219 which has an embossment pattern 201 in the cover 214. At the sides of the cover 214, outside of the embossment pattern 201, there are first register elements 218a, in the form of retention holes 218a, introduced into the cover 214. By virtue of the retention holes 218a it is possible to place the cover 214 on the compressed-air chamber 228 with precise registration. FIG. 6 shows the counterpiece to the cover 214 of the compressed-air press 219: the compressed-air chamber 228. The compressed-air chamber 228 has two register elements 218b in the form of retention elements 218b, attached so as to register with the retention holes 218a. A rubber ring 230 has also been introduced within the compressed-air chamber 228 and, when the compressed-air chamber 228 has been sealed by the cover 214, keeps the compressed-air press 219 airtight, in order that the air pressure introduced through the compressed-air connection 232 in the compressed-air chamber 228 can be maintained. To impress an embossment 202 into an aluminum foil 100, 106, the aluminum foil 100, 106 is positioned on to the compressed-air chamber 228, and the compressed-air chamber 228 is sealed by the cover 214, so that the aluminum foil 100, 106 is between the cover 214 and the rubber ring 230 or the base of the compressed-air chamber 228. Pressure on the aluminum foil 100, 106 is produced by introducing gas, for example in the form of air, through the compressed-air connection 232 and the air inlet 236 of the chamber 228 into the compressed-air chamber 228, and forces the aluminum foil 100, 106 on to the embossment pattern 201 of the cover 214. A vent 218 in the cover 214 allows the air compressed into the system to escape from the compressed-air chamber 228 by way of the cover 214. The material of the compressed-air press 219 should be selected in such a way that it withstands the superatmospheric pressure during the embossing process. By way of example, the cover 214 and the chamber 228 can have been manufactured from steel or aluminum, as in this example.

FIG. 1b shows the procedure for the pressing of a pre-embossed aluminum foil 107. This can be an aluminum foil 100 or an aluminum/polymer composite 106. In this example it is an aluminum/polymer composite 106. To this end, a polyester (20% Vitel® 2200B solution in ethyl methyl ketone from Bostik, with from 10 to 25% by weight of $MoS_2$) is applied by doctoring to an aluminum foil 100 and is then dried for 5 minutes at 100° C. The drying can also be undertaken at lower or higher temperatures, preferably from 20 to 200° C. A doctor used can by way of example, as here, be a steel doctor bar made of V2a steel with dimensions 1*5*30 cm, on a granite table. As an alternative, the polymer layer 104 can be applied by any process known to the person skilled in the art, for example spraying, rolling, brushing, transfer processes, use of a doctor wire or of a doctor roller, screen printing, dipcoating, gravure-roll methods, etc. An aluminum foil was thus produced with a 4 µm-thick polymer layer 104. In the case of the press procedure shown in the diagram of FIG. 1b, the aluminum foil 100 or the aluminum/polymer composite 106 is pressed between a ram 200 and a press mold 204. The press mold here can take the form of a container or can take the form of a ring. Since only the region with the embossments 202 are pressed by the ram 200 into the press mold 204, the interior of the aluminum foil 100 or of the aluminum/polymer composite 106 can have been designed without embossment pattern 201. During the press procedure, the ram 200 moves in the direction of the arrow 206. The ram 200 or the milled component 212 of an embossing tool 210, from FIG. 2a, comes into contact here with at least one portion of the embossments 202 of the embossment pattern 201 on the aluminum foil 100 or 106. The foil 100 or the composite 106 is pressed together with the ram 200 into the press mold 204. The foil 100 or the composite 106 here is pressed through the gap 208 that forms between ram 200 and appropriately dimensioned mold 204. Another term used for this gap 208 is gap dimension 208. The aluminum foil 100 or the composite 106 can be pressed into the embossing tool 210 to different depths, depending on the gap dimension 208. The load-bearing capability also depends on the thickness of the aluminum foil 100 or the composite 106, for which the abbreviated term foil 100, 106 is used below, and also on the shape and depth of the embossing pattern 201.

Figure 2B:
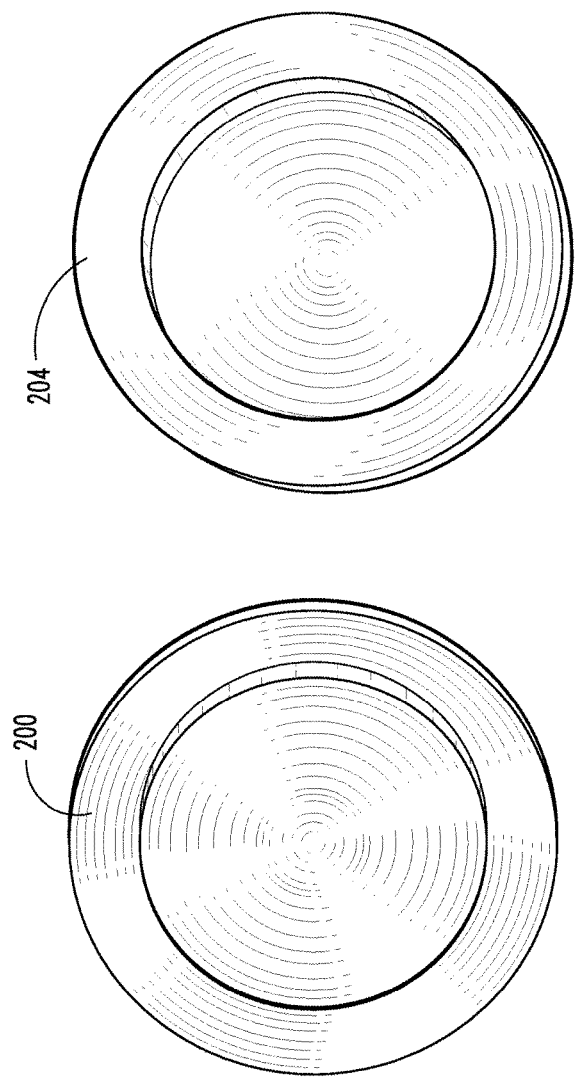
FIG. 2b is a photograph of a forming press with ram and press mold.
Figure 2C:
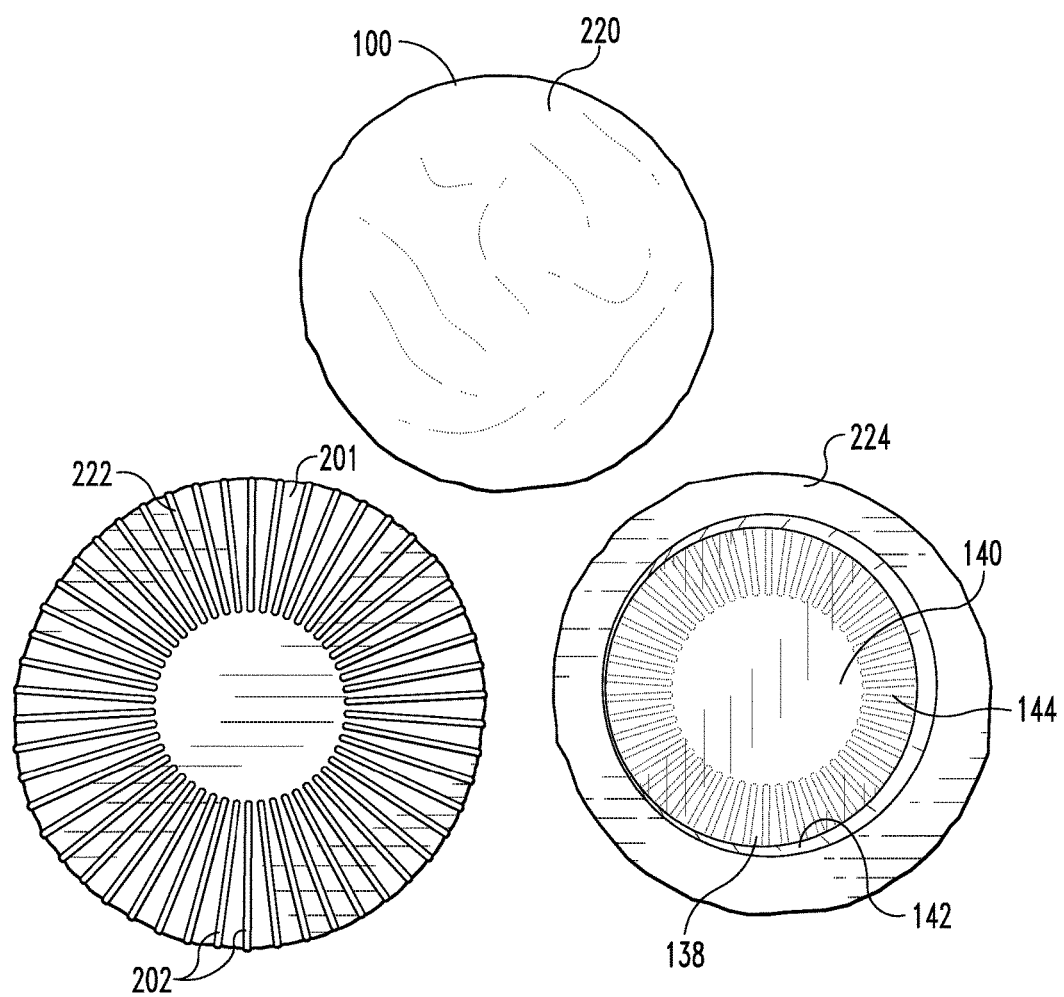
FIG. 2c is a photograph of an untreated aluminum foil, of an embossed aluminum foil, and of a pressure-formed aluminum foil container.
Figure 2D:
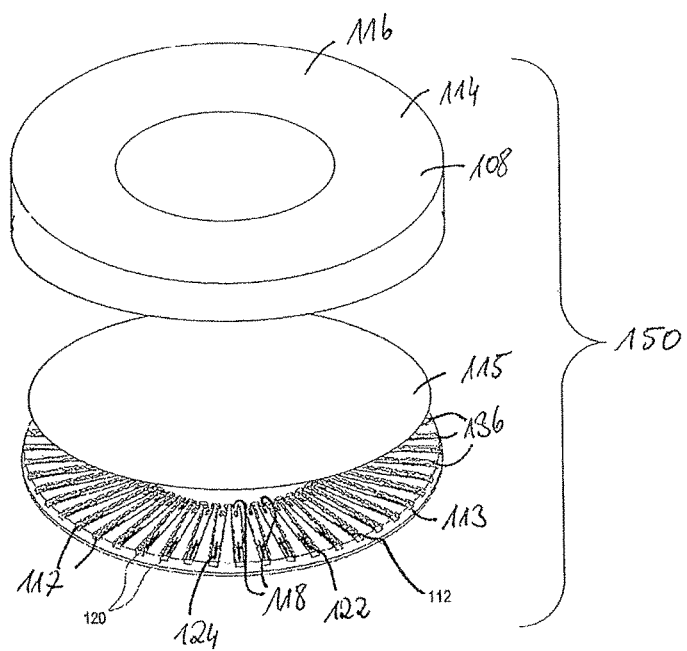
FIG. 2d is a diagram of a holder covered with a pressure-formed foil and comprising analytical aids.

FIG. 2b shows an example of a round ram 200 and of a corresponding press mold 204. FIG. 2c shows an example of the conversion of an untreated aluminum foil 100, 220 in the form of a circular untreated aluminum foil 220 into an embossed aluminum foil 222 and further conversion to a pressure-formed aluminum foil 224. When said untreated aluminum foil 220, which initially has been neither embossed nor pressed, takes the form of embossed foil 222 it has an embossment pattern 201. As previously described in relation to FIG. 1b, this embossment pattern 201 is completely removed from the foil 220 by pressing in the press procedure. After pressing, the aluminum foil 100, 224 is an aluminum foil with depression 104 in the form of a container 146. Said container 146 has a base 144, the shape of which corresponds to the press mold 204. The pressed depth 142 in this example is about 3 mm. The base 144 of the aluminum foil with depression 140 can be subjected to further mechanical processing, for example a cutout process. By this means it is possible to adapt the base to the shape of a holder 113, as shown in FIG. 2d. It is moreover possible to use a press mold 204 and a ram 200 which has a shape other than that shown in FIG. 2c, so that more than one depression can be introduced into the aluminum foil 100, 106.

FIG. 2d shows how the aluminum foil with depression 104 is used to cover, at least to some extent, a holder 113 with at least one analytical aid 112. The aluminum foil 100, 106 here can have a further polymer layer 114. The holder 113 here can have been molded from a single piece or, as shown here, can be composed of two elements 113 and 115. Alongside the holder 113 in which the cutouts 134, with at least one wall 136, have been introduced for the analytical aids 112, there can also be a holder cover 115 provided, which by way of example is bonded to the holder by way of a laser-welding process. The two elements 113 and 115 can also be bonded to one another by way of another process, for example an adhesive process. There are therefore only a few remaining apertures 117 and 118 present in the holder 113 that have to be sealed in order to achieve leakproof sterile sealing of the analytical aids 112 located in the cutouts 134. At least one available aperture 117 and optionally a second aperture 118 of the holder 113 is/are covered here. The aluminum foil 100, 106 can be exposed to tension during the protective covering of the apertures 117, 118, so that the aluminum foil 100, 106 then again has an almost smooth surface. Residual embossments 202 that have not been entirely removed by the press procedure in FIG. 1b can be rendered smooth by tension here. Once the apertures 117 and 118 have been covered by the aluminum foil, the aluminum foil is fused by way of a heat-sealing process to the holder 113 to give the container 146. It is thus possible to enclose the analytical aids 112 hermetically within the packaging 250.

The analytical aid 112 in FIG. 2d comprises at least one puncture element 120 or one test field 122, or both. In the example shown in FIG. 2d, the circular analytical aid 112 comprises a plurality of puncture elements 120 in the form of lancets 120, and a plurality of test fields 122. In this example, the test fields 122 and lancets 120 have respectively been accommodated together in a plurality of cutouts 134. One preferred embodiment has in each case one lancet 120 and one test field 122 arranged in such a way with respect to one another as to permit transfer of a liquid adhering to the lancet 120 on to the test field 122. This can be achieved, as in this example, by an arrangement which mutually superposes the lancet 120 and the test field 122, so that when slight pressure is exerted on the lancet 120 or test field 122 the liquid, in this example the blood, can be transferred to the test field 122. In an alternative embodiment, not shown here, a capillary with a hydrophilic coating 124 connects the lancet 120 and the test field 122. This example involves a microsampler as analytical aid 122. All of the embodiments described preferably have the analytical aids 122 held together in a ring-shaped holder 113 with cutouts 134.

Figure 2E:
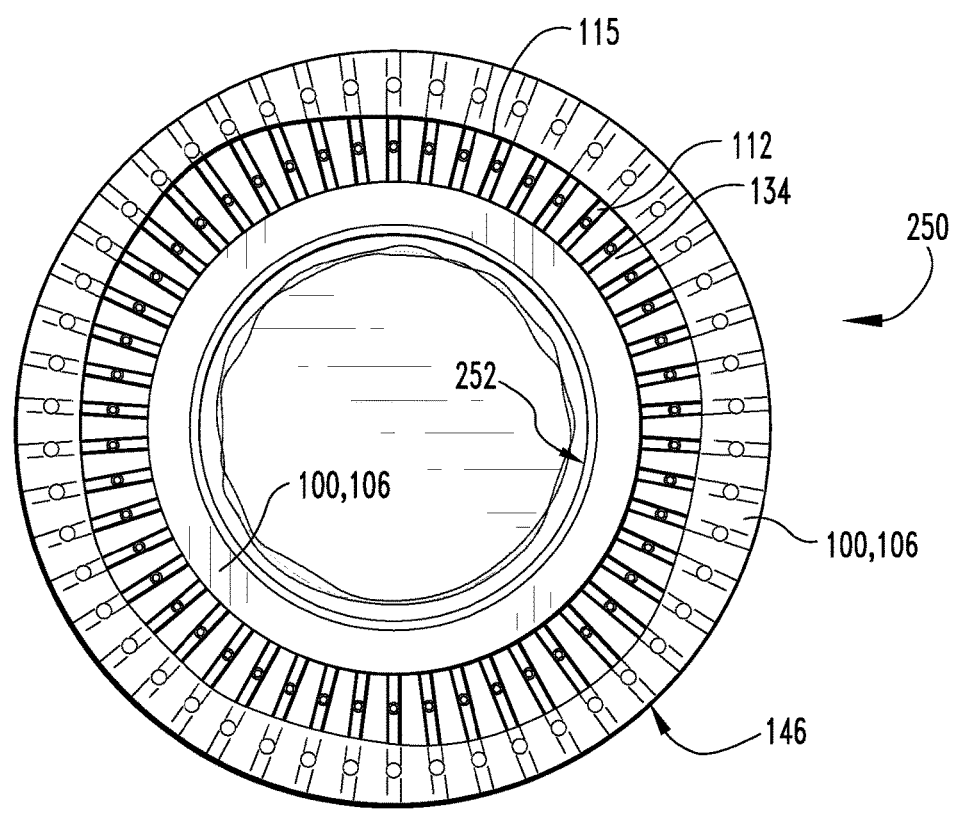
FIG. 2e is a photograph of a holder sealed with two pressed foils; these together with the holder form a container for analytical aids.
Figure 3:
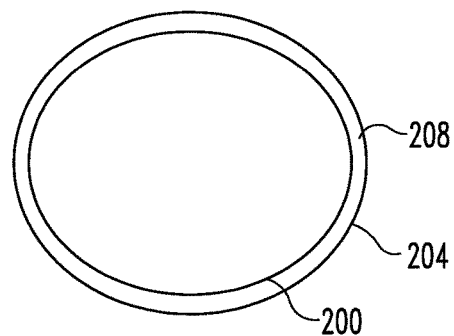
FIG. 3 is a diagram of a press tool with a ram located in the press mold, where these together define a gap dimension.

FIG. 2e shows a finished circular container 146 which takes the form of packaging 250 and which comprises an aluminum foil 100, 106 not only on the internal side 252 of the circle but also on the external side 254 of the circle. The analytical aids 122 arranged in a circle can be discerned between the two aluminum foils 100, 106, and have been introduced in the cutouts 134. The aluminum foils 100, 106 protectively cover a portion of the analytical aids 112. On the internal side 252 of the holder 113, there is preferably a pressed aluminum foil 100, 106 stretched over the aperture 118. Both aluminum foils 100, 106 have been fused by way of a heat-sealing process to the holder 113. To this end, at least one polymer layer 104 has been arranged on the aluminum foil 106 in a direction toward the holder 113, in order to permit fusion to the material of the holder 113 on heating. The heat-sealing process can, as in this example, be carried out at from 200 to 210° C. and from 150 to 160 bar, distributed across the foil, for a period of from 0.1 to 1.5 seconds.

Figure 4A:
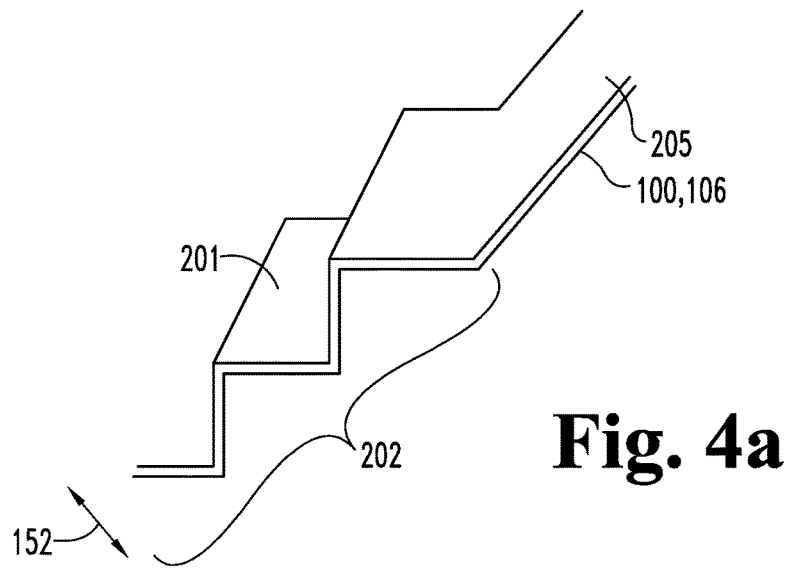
FIG. 4a is a diagram of an angular embossment pattern in an aluminum foil.
Figure 4B:
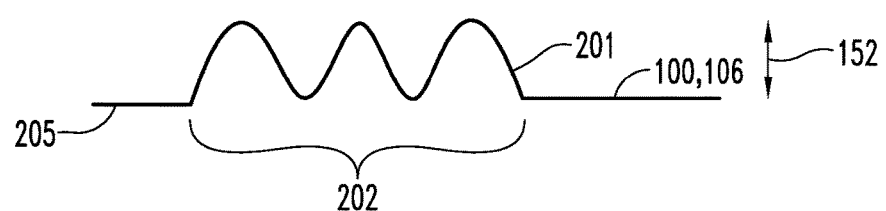
FIG. 4b is a diagram of a corrugated embossment pattern in an aluminum foil.

FIGS. 4a and 4b show an embossment pattern 201 on an aluminum foil 100, which has embossments 202. The number of embossments 202 present can also be greater or smaller than shown in FIG. 4a. Another possible design of the embossment pattern 201, alongside the zig-zag embossment pattern 201 in FIG. 4a, is by way of example a corrugated design, as shown in FIG. 4b. This embossment pattern 201 gives the aluminum foil 100 a maximal cross section 152 differing from that of the unembossed aluminum foil 100 in FIG. 1a, since material is displaced by the embossing process. The thickness of the foil 100 preferably remains constant here.

While exemplary embodiments have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

| | Key |
|---|---|
| 100 | Aluminum foil |
| 101 | First side |
| 102 | Second side |
| 104 | First polymer layer/foil |
| 106 | Aluminum/polymer composite |
| 107 | Preembossed foil |
| 108 | Wax layer |
| 112 | Analytical aid |
| 113 | Holder |
| 114 | Further polymer layer/protective coating material |
| 115 | Cover of holder |
| 116 | Packaging constituent |
| 117 | Aperture |
| 118 | Second aperture |
| 120 | Puncture element, lancet |
| 122 | Test field |
| 124 | Hydrophilic coating |
| 134 | Cutout |
| 136 | Wall |
| 138 | Depression |
| 140 | Aluminum foil with depression |
| 142 | Pressed depth |
| 144 | Base of depression |
| 146 | Container |
| 148 | Sheet-like composite material |
| 150 | Packaging |
| 152 | Maximal cross section |
| 200 | Ram |
| 201 | Embossment pattern |
| 202 | Embossment |
| 203 | Circular area |
| 204 | Press mold |
| 205 | Sheet-like aluminum foil |
| 206 | Press direction |
| 208 | Gap/gap dimension |
| 210 | Embossing tool |
| 212 | Milled component |
| 214 | Cover |
| 216 | Foam |
| 218 | Vent |
| 218a | Retention hole/first registration element |
| 218b | Retention element/second registration element |
| 219 | Compressed-air press |
| 220 | Untreated aluminum foil |
| 222 | Embossed aluminum foil |
| 224 | Pressure-formed aluminum foil |
| 228 | Compressed-air chamber |
| 230 | Rubber ring |
| 232 | Compressed-air connection |
| 234 | Base of compressed-air chamber |
| 236 | Air inlet |
| 250 | Packaging |
| 252 | Internal side of circle |
| 254 | External side of circle |

What is claimed is:
1. A container, comprising:
a sheet of composite material comprising a pressed or deep-drawn aluminum foil with first and second surface sides and a first polymer layer bonded to at least one of the two surface sides; and a holder having an aperture and a cutout that accepts an analytical aid, the composite material and the holder together forming the container;

wherein the aluminum foil with the first polymer layer bonded thereto comprises two surfaces angled relative to one another, the two surfaces forming a depression that corresponds to the shape of the holder, one of the two surfaces covering the aperture.

2. The container as claimed in claim 1, wherein the first polymer layer comprises a thermoplastic polymer.

3. The container as claimed in claim 2, wherein the thermoplastic polymer is a polyester.

4. The container as claimed in claim 3, wherein the polyester is selected from the group consisting of polycarbonate, polyethylene naphthalate, polybutylene terephthalate, polyethylene terephthalate, and polyester resin, and mixtures of at least two thereof.

5. The container as claimed in claim 1, wherein the aluminum foil has a thickness of between 10 to 30 μm.

6. The container as claimed in claim 1, wherein the composite material includes a further polymer layer.

7. The container as claimed in claim 1, wherein the analytical aid comprises a puncture element or a test field or both, for the detection of an analyte in a body fluid.

8. The container as claimed in claim 1, wherein the analytical aid comprises a hydrophilic coating.

9. The container as claimed in claim 1, wherein the first polymer layer is hydrophilic.

10. The container as claimed in claim 1, wherein the first polymer layer has a thickness in the range from 0.5 to 10 μm.

11. The container as claimed in claim 1, wherein the first polymer layer has a thickness in the range from 2 to 8 μm.

12. The container as claimed in claim 1, wherein the thickness of the first polymer layer is in the range from 3 to 6 μm.

13. The container as claimed in claim 1, wherein the container is made from an aluminum foil with at least one embossment.

14. The container of claim 1, wherein the angle between the two surfaces is between 30° and 150°.

15. The container of claim 1, wherein the depression has a depth of between 2 to 7 mm.

16. A process for the production of a container for the storage of analytical aids, comprising:

providing a holder with a plurality of analytical aids;

protectively covering at least one portion of the holder with a sheet of composite material including an aluminum foil bonded to a polymer layer, wherein the polymer layer faces toward the holder; and heating the polymer layer so that the polymer layer melts at least to some extent and bonds to the holder and forms a container, wherein, prior to or during the process of protectively covering at least one portion of the holder with the sheet of composite material, the aluminum foil is pressed or deep-drawn.

17. The process as claimed in claim 16, wherein the polymer layer comprises a thermoplastic polymer.

18. The process as claimed in claim 17, where the thermoplastic polymer is a polyester.

19. The process as claimed in claim 18, where the polyester is one selected from the group consisting of: polycarbonate, polyethylene naphthalate, polybutylene terephthalate, polyethylene terephthalate, and polyester resin, and mixtures of at least two thereof.

20. A container, comprising:

a sheet of composite material comprising a pressed or deep-drawn aluminum foil with first and second surface sides and a first polymer layer bonded to at least one of the two surface sides, the first polymer layer comprising molybdenum sulfide ($MoS_2$); and a holder having an aperture and a cutout that accepts an analytical aid, the composite material and the holder together forming the container;

wherein the aluminum foil with the first polymer layer bonded thereto covers the aperture.

* * * * *